United States Patent
Barnea et al.

(10) Patent No.: US 12,130,219 B2
(45) Date of Patent: Oct. 29, 2024

(54) METHOD AND SYSTEM FOR EVALUATING FERTILITY OF HUMAN SPERMATOZOA

(71) Applicant: TECHNOLOGY INNOVATION MOMENTUM FUND (ISRAEL) LIMITED PARTNERSHIP, Tel Aviv (IL)

(72) Inventors: Itay Barnea, Petach Tikva (IL); Natan Tzvi Shaked, Mazkeret Batya (IL); Lidor Karako, Tel Aviv (IL); Michal Balberg, Tel Aviv (IL); Alon Shalev, Tel Aviv (IL)

(73) Assignee: TECHNOLOGY INNOVATION MOMENTUM FUND (ISRAEL) LIMITED PARTNERSHIP, Tel Aviv (IL)

( * ) Notice: Subject to any disclaimer, the term of this patent is extended or adjusted under 35 U.S.C. 154(b) by 1090 days.

(21) Appl. No.: 16/967,033

(22) PCT Filed: Jan. 30, 2019

(86) PCT No.: PCT/IL2019/050118
§ 371 (c)(1),
(2) Date: Aug. 3, 2020

(87) PCT Pub. No.: WO2019/150365
PCT Pub. Date: Aug. 8, 2019

(65) Prior Publication Data
US 2021/0041336 A1    Feb. 11, 2021

Related U.S. Application Data (60) Provisional application No. 62/625,040, filed on Feb. 1, 2018.

(51) Int. Cl.
| | | |
|---|---|---|
| G01N 15/0205 | (2024.01) | |
| G01N 33/487 | (2006.01) | |
| G02B 21/00 | (2006.01) | |

(52) U.S. Cl.
CPC ... *G01N 15/0205* (2013.01); *G01N 33/48735* (2013.01); *G02B 21/0056* (2013.01); *G02B 21/0076* (2013.01)

(58) Field of Classification Search
None
See application file for complete search history.

(56) References Cited

U.S. PATENT DOCUMENTS

| | | |
|---|---|---|
| 8,842,901 B2 | 9/2014 | Ozcan et al. |
| 2004/0089798 A1 | 5/2004 | Gruber et al. |
| 2009/0125242 A1 | 5/2009 | Choi et al. |
| 2015/0031019 A1 | 1/2015 | Nordbo et al. |
| 2015/0049343 A1 | 2/2015 | Shaked et al. |

FOREIGN PATENT DOCUMENTS

| | | |
|---|---|---|
| CN | 1774623 | 5/2006 |
| JP | 2005521425 | 7/2005 |
| WO | 13140396 A1 | 7/2013 |
| WO | 03085379 A3 | 10/2013 |
| WO | 2016/178234 A1 | 11/2016 |

OTHER PUBLICATIONS

Cohen-Bacrie P, Belloc S, Ménézo YJ, Clement P, Hamidi J, Benkhalifa M. Correlation between DNA damage and sperm parameters: a prospective study of 1,633 patients. Fertil Steril. May 2009;91(5):1801-5 (Year: 2009).*
Jayaraman, V., Upadhya, D., Narayan, P.K. et al. Sperm processing by swim-up and density gradient is effective in elimination of sperm with DNA damage. J Assist Reprod Genet 29, 557-563 (2012) (Year: 2012).*
Mattanovich, D., Borth, N. Applications of cell sorting in biotechnology. Microb Cell Fact 5, 12 (2006) (Year: 2006).*
Henkel, R.R., Schill, WB. Sperm preparation for ART. Reprod Biol Endocrinol 1, 108 (2003) (Year: 2003).*
Haifler M, Girshovitz P, Band G, Dardikman G, Madjar I, Shaked NT. Interferometric phase microscopy for label-free morphological evaluation of sperm cells. Fertil Steril. Jul. 2015;104(1):43-7.e2. (Year: 2015).*
Di Caprio G, Ferrara MA, Miccio L, Merola F, Memmolo P, Ferraro P, Coppola G. Holographic imaging of unlabelled sperm cells for semen analysis: a review. J Biophotonics. Oct. 2015;8(10):779-89 (Year: 2015).*
Poola, Praveen Kumar, et al. "Quantitative label-free sperm imaging by means of transport of intensity." Quantitative Phase Imaging II. vol. 9718. SPIE, 2016. (Year: 2016).*
Crha, Igor et al. "Digital holographic Microscopy in human sperm imaging", J Assist Reprod Genet (2011) 28:725-729.
Di Caprio et al., "4D tracking of clinical seminal samples for quantitative characterization of motility parameters", Biomedical Optics Express, Mar. 2014, vol. 5, No. 3, pp. 690-700.

(Continued)

*Primary Examiner* — John S Brusca
*Assistant Examiner* — Jonathan Edward Hayes
(74) *Attorney, Agent, or Firm* — BROWDY AND NEIMARK, P. L. L. C.

(57) ABSTRACT

Methods and systems for evaluating fertility potential of a living sperm cell are presented and involve providing a predetermined classification function correlating between one or more physio spatial parameters of sperm cells and DNA fragmentation distribution in sperm cells, providing data indicative of the one or more physio spatial parameters of the living sperm cell, and applying the classification function to the one or more physio spatial parameters of the living sperm cell to thereby determine a DNA fragmentation level, inside the DNA fragmentation distribution, in the living sperm cell, the DNA fragmentation level being indicative of the fertility potential of the living sperm cell.

14 Claims, 6 Drawing Sheets

(56) References Cited

OTHER PUBLICATIONS

E. Patrascu et al: "Optimized Morphologic evaluation of biostructures by examination in polarized light and differential interference contrast microscopy", Leg Med 122j 275-282 (2014).
Digital Holographic Microscopy and Study on Application Technology—(EN translation from CN attached) Translation of Relevantasic science series of China Doctor's Theses Full-text Database, Basic Science Series, Apr. 15, 2015.
Di Caprio et al. "Quantitative Label-Free Animal Sperm Imaging by Means of Digital Holographic Microscopy", IEEE Journal of Selected Topics in Quantum Electronics, vol. 16, No. 4, Jul./Aug. 2010.
Boland et al., Automated Recognition of Patterns Characteristics of Subcellular Structures in Fluorescence Microscopy Images, Cytomertry 33:366-375, 1998.
Huszar G et al: "Fertility testing and ICSI sperm selection by hyaluronic acid binding: clinical and genetic aspects", Reproductive Biomedicine Online, Elsevier, Amsterdam, NL, vol. 14 No. 5. Jan. 1, 2007. (Jan. 1, 2007), pp. 650-663.

\* cited by examiner

METHOD AND SYSTEM FOR EVALUATING FERTILITY OF HUMAN SPERMATOZOA

TECHNOLOGICAL FIELD

The invention relates generally to systems and methods of analysis of biological cells and organisms. Specifically, the invention is useful for optical analysis of label-free sperm cells.

BACKGROUND

DNA fragmentation in sperm is considered to be one of the main causes of the low success rate of intracytoplasmic sperm injection (ICSI) for couples facing infertility.

DNA fragmentation in sperm, defined as the breaking of the DNA coil into single or double-stranded fragments, has long been associated with an impaired ability for spontaneous pregnancy, as well as with difficulties in achieving live births after artificial reproductive technology (ART) procedure. It has been shown that couples undergoing conventional in vitro fertilization (IVF) and intracytoplasmic sperm injection (ICSI) where the sperm donor is diagnosed with high percentage of DNA fragmented sperms experience low pregnancy rates, abnormal embryo development and increase miscarriages. DNA fragmentation is not only an important factor in the failure of ICSI cycles involving men with fertility problems, but also those involving men with normal sperm. Reports have shown that in normal semen samples between 20%-30% of sperm cells have fragmented DNA. Moreover, as fertility treatments are becoming more frequent in men in their forties and fifties, the quality of sperm decreases compared to the sperm of younger men, as it has been shown that DNA fragmentation increases with age.

There are several methods for the evaluation of DNA fragmentation. These include: the transferase dUTP nick end labeling (TUNEL) test, which evaluates DNA fragmentation by staining the terminal end of nucleic acids; the Comet test, which evaluates DNA strand breaks by electrophoresis of the cell content; and the sperm chromatin dispersion assay (SCD), which evaluates DNA fragmentation by the presence or absence of halo around the cell head. Acridine orange (AO) dye method is used as well, which differentiates between double stranded (dsDNA) and single-stranded DNA (ssDNA) or RNA. In this method, dsDNA emits green fluorescence and single-stranded DNA or RNA emits red fluorescence, and fluorescent microscopy or flow cytometry is used to evaluate the different colors.

Most of the methods for the evaluation of DNA fragmentation listed above require killing of the cells. This renders them irrelevant for the assessment of the DNA integrity of the individual live sperm cells used in ICSI. Today, the selection of sperm cells for ICSI is performed using the limited capabilities of relatively low-magnification brightfield microscopy (BFM), usually with 200-400× total magnification. This tool enables the embryologist to select motile sperm on the basis of basic morphological characteristics, such as the sperm head size. Another recent method for sperm selection is intracytoplasmic morphologically selected sperm injection (IMSI). In this method the sperm is imaged using mostly digital magnifications of 6300× or higher, where the cells are imaged without staining using differential interference contrast (DIC). Due to the higher magnification and enhanced contrast of the IMSI systems, the embryologist can observe morphological characteristics such as cytoplasmic vacuoles.

GENERAL DISCRIPTION

The present invention provides a novel technique for determining the fertility potential of a sperm cell, without the need to stain the sperm cell, thereby enabling on-line selection of a live sperm cell, e.g. for IVF and ICSI procedures. The fertility of the sperm cell can be determined based on the DNA fragmentation state of the sperm cell which is determined based on morphological, physio-spatial, parameters of the sperm cell.

According to the invention, there is a correlation between certain physio-spatial parameter(s) of the sperm cell and the DNA fragmentation state of the sperm cell. By knowing the value(s) or the value range(s) of certain physio-spatial parameter(s) of the sperm cell and/or by correlating between the values, or ranges of values, of two or more physio-spatial parameters, the cell's DNA fragmentation condition can be determined which then enables determining the sperm cell's fertility potential.

Thus, according to the invention there is provided a classifier of the sperm cell's fertility potential based on the sperm cell's DNA fragmentation level. The input to the classifier is indicative of one or more physio-spatial parameters of the sperm cell, and the output is indicative of the DNA fragmentation level and/or the fertility potential of the sperm cell. The classifier can be defined by one or more correlation functions relating the one or more physio-spatial parameters of the sperm cell with the DNA fragmentation level of the sperm cell. The physio-spatial parameters of the sperm cell are obtained from 2D and/or 3D images of the sperm cell. In some embodiments, the physio-spatial parameters of the sperm cell are obtained by quantitative phase microscopy imaging techniques, such as Interferometric Phase Microscopy (IPM) which is used as a non-limiting example in the description herein below.

According to the invention, determination of the DNA fragmentation level of a sperm cell is done by firstly defining a DNA fragmentation distribution. The DNA fragmentation distribution can be defined based on several known DNA fragmentation assay techniques as will be further detailed below. Then, one fragmentation level from the distribution is assigned to the sperm cell based on the sperm cell's physio-spatial parameter(s). The classifier can be trained to assign the DNA fragmentation level to the sperm cell, for every DNA fragmentation distribution used, by building a DNA fragmentation database utilizing sperm samples which their fragmentation level is determined by one of the DNA fragmentation assay techniques, and correlating between the physio-spatial parameter(s) of the sperm cell and its DNA fragmentation level (that defines its fertility potential).

In other words, determination of the DNA fragmentation level of a non-stained sperm cell is achieved by firstly generating a classification mechanism, which correlates between physio-spatial characteristics of said sperm cells, obtained for example using QPM on said non stained sperm cell, and two or more DNA fragmentation levels, obtained following staining said same sperm cell for a selected DNA fragmentation assay and evaluating its DNA fragmentation level via said selected assay. In some embodiments of the present invention, such generation of said classification mechanism may comprise of a training phase and a validation phase, while said training phase utilizes aposteriori (i.e. retrospective) data provision into said classification mechanism, and while said validation phase utilizes apriori (i.e.

prospective) data provision into said classification mechanism, in order to evaluate the performance of said classification mechanism. Once said classification mechanism has been generated, the classification mechanism is used on a non-stained sperm cell, which would allow evaluating a DNA fragmentation level of the non-stained sperm cell, while still allowing using the sperm cell for example for its subsequent injection into an oocyte, or for conventional IVF.

It should be noted that the term of "living sperm cell", as used herein, means a living, motile (free to move, not-fixed), and label-free (not-stained) sperm cell.

In accordance with one embodiment of the present invention, the DNA fragmentation state of a specific sperm cell can be classified into one of two levels, i.e. a Boolean result. Under this particular embodiment of the present invention, QPM information that was acquired on live, individual sperm cells, in conjunction with the fragmentation state that was thereafter measured on the same sperm cells using terminal deoxynucleotidyl transferase-mediated deoxyuridine triphosphate-nick end labeling (TUNEL) assay, would subsequently be used to train a classification algorithm that would thereby resemble the performance of the TUNEL assay, on non-stained cells.

In accordance with yet another embodiment of the present invention, the DNA fragmentation level can be classified to one out of plurality of distinct fragmentation levels, e.g. five levels when using Acridine Orange (AO) assay. Under this particular embodiment of the present invention, QPM information that was acquired on live, individual sperm cells, in conjunction with the fragmentation state that was thereafter measured on the same sperm cells using the Acridine Orange (AO) assay—whose results are hereinafter presented in length—would subsequently be used to train a classification algorithm that would thereby resemble the performance of the AO assay, on non-stained cells.

Under yet other embodiments of the present invention, QPM information that would be acquired on live, individual sperm cells, in conjunction with the fragmentation state that was thereafter measured on the same sperm cells using either of the following assays: (i) single cell gel electrophoresis, also known as comet assay (SCGE), (ii) sperm chromatin dispersion (SCD), or (iii) sperm chromatin structure assay (SCSA), would subsequently be used to train a classification algorithm that would thereby resemble the performance of either the SCGE, the SCD, or the SCSA assay, respectively, on non-stained cells.

Thus, according to a broad aspect of the invention, there is provided a method for evaluating fertility potential of a living sperm cell, the method comprising:

Providing a predetermined classification function correlating between one or more physio spatial parameters of sperm cells and DNA fragmentation distribution in sperm cells;

Providing data indicative of said one or more physio spatial parameters of the living sperm cell; and Applying said classification function to said one or more physio spatial parameters of the living sperm cell to thereby determine a DNA fragmentation level, inside said DNA fragmentation distribution, in said living sperm cell, the DNA fragmentation level being indicative of the fertility potential of the living sperm cell.

In some embodiments, the step of providing data indicative of said one or more physio spatial parameters of the living sperm cell comprises measurement of said living sperm cell with quantitative phase microscopy (QPM).

In some embodiments, the step of providing data indicative of said one or more physio spatial parameters of the living sperm cell comprises measurement of said living sperm cell with interferometric phase microscopy (IPM).

In some embodiments, the DNA fragmentation distribution is a binary distribution comprising two levels of DNA fragmentation being respectively indicative of fertile and non-fertile conditions of a sperm cell.

In some embodiments, the DNA fragmentation distribution is a multi-class distribution comprising at least three levels of DNA fragmentation being indicative of respective fertility potential levels of a sperm cell.

In some embodiments, the DNA fragmentation distribution is defined based on one of the following DNA fragmentation assays: (a) acridine orange (AO), (b) terminal deoxynucleotidyl transferase-mediated deoxyuridine triphosphate-nick end labeling (TUNEL), (c) single cell gel electrophoresis (SCGE), (d) sperm chromatin dispersion (SCD), and (e) sperm chromatin structure (SCSA).

In some embodiments, the predetermined classification function is determined by providing a dataset of training sperm cell samples each having its measured one or more physio spatial parameters, and their respective DNA fragmentation levels derived from a DNA fragmentation assay.

In some embodiments, the one or more physio spatial parameters comprise(s) surface area of the living sperm cell or of an organelle thereof.

In some embodiments, the one or more physio spatial parameters comprise(s) dry mass of the living sperm cell or of an organelle thereof.

In some embodiments, the one or more physio spatial parameters comprise(s) an average optical path delay of said sperm cell, or of an organelle thereof.

In some embodiments, the one or more physio spatial parameters comprise(s) a variance of optical path delay being calculated over surface area of said sperm cell, or of an organelle thereof.

In some embodiments, the organelle comprises one or more of the following: head, nucleus, acrosome and tail of the living sperm cell.

In some embodiments, the one or more physio spatial parameters comprise a subtraction between an average optical path delay calculated upon an anterior portion of head of said sperm cell and an average optical path delay calculated upon a posterior portion of the head of said sperm cell, wherein each of said anterior and posterior portions comprises between 40 and 60 percent of surface area of the head of said sperm cell.

In some embodiments, the living sperm cell has passed through one of the following assays before measuring its said one or more physio-spatial parameters: (a) sperm density gradient, (b) swim-up, (c) hyaluronic acid binding, and (d) magnetic sorting using annexin V microbeads.

In some embodiments, the sperm cell is a washed sperm cell.

In some embodiments, the method further comprises determining whether said living sperm cell fulfils a standardized criteria for selection of sperm cells in a fertilization procedure. The standardized criteria may comprise criteria from World Health Organization (WHO) laboratory manual(s) for the examination and processing of human semen.

A method for use in an in vitro fertilization (IVF) procedure is also provided. The method comprising:
providing a plurality of sperm cells;
applying any of the above-mentioned methods to each sperm cell and evaluating/determining its fertility potential; and selecting each sperm cell that has a fertility potential that meets a standardized criteria for selection of sperm cells in the IVF procedure.

According to another broad aspect of the invention, there is provided a system for evaluating fertility potential of a living sperm cell, the system comprising:

a data input utility configured and operable for receiving a first input data indicative of a classification function correlating between one or more physio spatial parameters of sperm cells and DNA fragmentation distribution in sperm cells, and a second input data indicative of said one or more physio spatial parameters of the living sperm cell;

a processing utility configured and operable for processing said first and second data and determine a DNA fragmentation level, inside said DNA fragmentation distribution, in said living sperm cell, the DNA fragmentation level being indicative of the fertility potential of the living sperm cell, and generating a corresponding output data; and a data output utility configured and operable to present the output data to a user of the system.

In some embodiments, the system further comprises a measurement system configured to measure said living sperm cell and determine said one or more physio spatial parameters of the living sperm cell. The measurement system may be a quantitative phase microscopy system configured and operable to measure optical path delay (OPD) of one or more organelles of said living sperm cell to thereby determine said one or more physio spatial parameters of the living sperm cell.

In some embodiments, the processing utility is further configured and operable for determining whether said living sperm cell fulfils a standardized criteria for selection of sperm cells in a fertilization procedure.

An apparatus for use in an in vitro fertilization (IVF) procedure is also provided. The apparatus comprising:

a system for evaluating fertility potential of a living sperm cell as described above; and a sorting system configured and operable to: receive a plurality of living sperm cells, individually enable evaluating the fertility potential of each of the living sperm cells; and individually select one or more of the living sperm cells that meet a predetermined fertility potential score.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF SPECIFIC EMBODIMENTS

Figure 1:
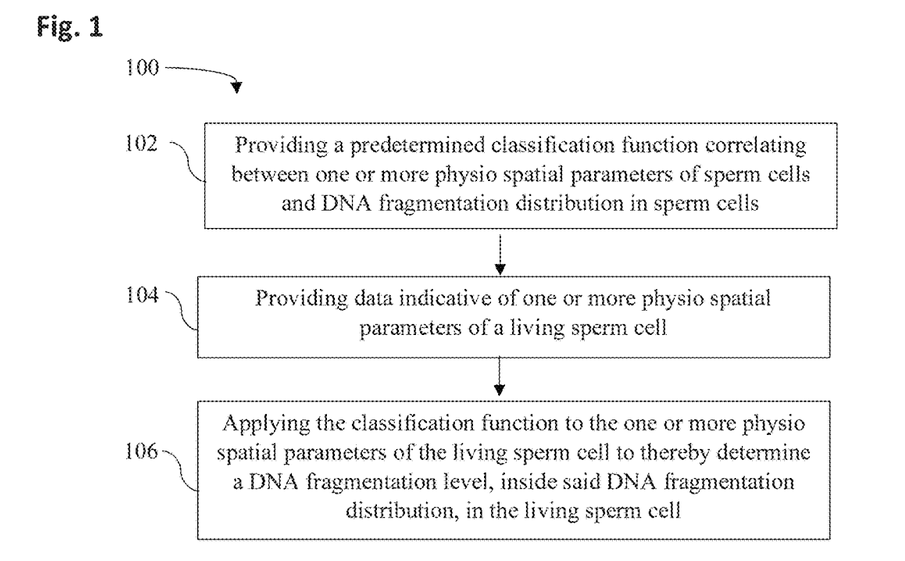
FIG. 1 illustrates a method for evaluating fertility potential of a sperm cell, according to some embodiments of the invention.

Reference is made to FIG. 1 illustrating a non-limiting example of a method 100 for evaluating fertility potential of a living sperm cell, in accordance with the present invention. The method of the invention is significant in that it enables determining the fertility potential of a living sperm cell in an on-line procedure, e.g. during selection of sperm cell candidates for use in fertilization procedures. The method 100 includes the following steps.

In step 102, a classification function (CF), (or "operation", as used herein interchangeably) that correlates between one or more physio spatial parameters of sperm cells and DNA fragmentation distribution in sperm cells is provided. The classification function can be readily provided, i.e. it is previously built as will be exemplified herein below. The classification function may receive an input and then generates a corresponding output.

In step 104, the input to the classification function, in the form of data indicative of the one or more physio spatial parameters (PSP) of the living sperm cell under inspection, is provided. The input data of the one or more physio spatial parameters can be provided by a variety of means known in the field. Specifically, as will be exemplified below, the data can be provided by conducting on-line measurements on the living sperm cell by the use of quantitative phase microscopy (QPM) techniques.

In step 106, the classification function is processed together with the input data of the one or more physio spatial parameters, e.g. by applying the classification function to the one or more physio spatial parameters of the living sperm cell, to thereby determine a DNA fragmentation level, inside the DNA fragmentation distribution, in the living sperm cell. It is already known that the DNA fragmentation level in one or more organelles of the sperm cell is indicative of the fertility potential of the sperm cell. The present invention may utilize any newly and specifically developed technique that correlates or matches between the DNA fragmentation state of the sperm cell at one side and the fertility of the sperm cell at the other side, or may utilize any known and established technique that teaches about the fertility of the sperm cell in light of its DNA fragmentation state. According to the invention, the output from running the classification function together with the one or more physio spatial parameters of the living sperm cell can be the quantitative DNA fragmentation level or the qualitative or quantitative fertility potential score of the living sperm cell, or both.

The provision of the one or more physio spatial parameters of the living sperm cell, in step 104, can be done by imaging the living sperm cell with quantitative phase microscopy (QPM), and in particular, by using interferometric phase microscopy (IPM), as was described for example, in WO16178234, co-assigned to the assignee of the present invention.

Quantitative phase microscopy (QPM), such as Interferometric phase microscopy (IPM), also known as digital holographic microscopy (DHM), is a stain-free imaging technique, which can capture both the amplitude and phase profiles of the light that passes through transparent biological cells. QPM provides a quantitative measurement of the optical path delay (OPD) at each point in the sample. OPD is defined as the difference between the refractive index of the sample and that of the surrounding medium multiplied by the sample thickness (see Equation 1 below). Thus, OPD has positive correlation both with the thickness and with the density on the sperm cell. The resulting OPD map is a visualization of a quantified contrast based on the thickness and density at all points of the cell, in contrast to differential interference contrast (DIC) microscopy, the basis of IMSI, which records OPD gradient and thus provides contrast only near the cell and organelle edges. In the above-mentioned WO16178234, it was shown that there is an agreement between the label-free IPM images and stained cells. The particular IPM module used was the i interferometer, which is a compact external module that can be positioned at the exit of a microscope and thus makes IPM much more accessible to fertility clinics.

OPD is defined as:

$$OPD(x, y) = [n_c(x, y) - n_m] \times h_c(x, y) \quad \text{Equation 1}$$

where OPD (x, y) is the OPD at point (x, y), $n_c$(x, y) is the integral refractive index of the sperm cells at point (x, y), $n_m$ is the refractive index of the medium and $h_c$(x, y) is the thickness of the cell at point (x, y).

Agreement between the information obtained by stain-free IPM of fixed unstained sperm cells and the information obtained by BFM of stained sperm cells, in connection with the measurement of key morphological parameters using the WHO guidelines, has been demonstrated. The fact that the IPM and BFM results are in agreement enables to assess the OPD maps in accordance to the WHO-2010 criteria, but without the use of staining.

Information obtained by morphological assessment of stain-free IPM images of sperm cells to categorization of DNA fragmentation by Acridine Orange staining of the same cells is compared herein below. Accordingly, stain-free IPM can be used to indicate DNA integrity of the individual sperm cells used in ICSI.

Based on the OPD measurement of the sperm cell, the one or more physio spatial parameters of the sperm cell may include a two-dimensional data of the sperm cell, e.g. surface area of the living sperm cell or of an organelle thereof. Additionally or alternatively, the one or more physio spatial parameters may include three dimensional data of the sperm cell, such as the dry mass of the living sperm cell or of an organelle thereof, as will be further described herein below with reference to FIGS. 4 to 7. In some embodiments, the one or more physio spatial parameters include an average optical path delay (average OPD) of the sperm cell, or of an organelle thereof. In some embodiments, the one or more physio spatial parameters include a variance of optical path delay being calculated over surface area of the sperm cell, or of an organelle thereof. In each of the possibilities above, the organelle of the sperm cell can be any internal organelle that can teach about DNA fragmentation in the sperm cell, such as but not limited to, the sperm's head, nucleus, acrosome and/or tail.

The OPD map of the cell head, nucleus and acrosome, in addition to many parameters that can be calculated based on the OPD, such as dry mass, mean anterior-posterior difference, head, acrosome, and nucleus areas, and head OPD variance, have various important implications with respect to the DNA fragmentation and the fertility of the sperm cell. The OPD variance has a strong connection to the presence or lack of a nucleus, and acrosome area is significant as it is the basis for one of the WHO criteria. Nucleus area is significant as a smaller nucleus may indicate a well-packed nucleus with less DNA fragmentation. The dry mass of the cell corresponds primarily to the protein concentration.

In accordance with some embodiments of the invention, the measurement of the one or more physio spatial parameters of the living sperm cell may be preceded by a step of passing the living sperm cell through one of the following assays: (a) sperm density gradient, (b) swim-up, (c) hyaluronic acid binding, and (d) magnetic sorting using annexin V microbeads.

The DNA fragmentation distribution used with the present invention can be a distribution derived by a known DNA fragmentation assay technique. Non-limiting examples include the following assays: (a) acridine orange (AO), (b) terminal deoxynucleotidyl transferase-mediated deoxyuridine triphosphate-nick end labeling (TUNEL), (c) single cell gel electrophoresis (SCGE), (d) sperm chromatin dispersion (SCD), and (e) sperm chromatin structure (SCSA). Specifically, while not limiting, the present invention is exemplified using the AO assay, as will be further described below. Alternatively, it is noted that the invention can be practiced with any newly developed (not yet known) DNA fragmentation distribution derived from a new DNA fragmentation assay.

In some embodiments, the DNA fragmentation distribution used with the invention can be a binary distribution (e.g., a yes/no decision), such that it includes two levels of fragmentation decisions, e.g. yes/no fragmentation corresponding to yes/no fertility potential of the sperm cell.

In some embodiments, the DNA fragmentation distribution used with the invention can be a multi-class distribution having a plurality of fragmentation levels, such that it includes at least three levels of fragmentation decisions corresponding to a plurality of (e.g. two or more) fertility potential scores of the sperm cell. For example, the AO assay, exemplified herein, generates five levels of DNA fragmentation that can be utilized for decision making with regards to the fertility potential of the sperm cell.

In some embodiments, though not specifically illustrated in the figure, the method 100 may further include a step for determining whether the living sperm cell fulfils a standardized criteria for selection of sperm cells in a fertilization procedure. In other words, the sperm cell is subjected to an additional examination, in addition to determining its DNA fragmentation level. The additional examination can be used in addition to the DNA fragmentation level in order to determine the fertility potential score of the sperm cell. For example, in one example, only if the sperm cell satisfies both the condition of the DNA fragmentation and the condition of the standardized criteria, it will be given a fertility potential score suitable for using the sperm cell in a fertilization procedure.

The standardized criteria may be a criteria selected from a World Health Organization (WHO) laboratory manual(s) for the examination and processing of human semen, such as the WHO2010 manual.

Accordingly, in some exemplary embodiments, the invention provides a method for use in an in vitro fertilization (IVF) procedure. The method includes providing a plurality of sperm cells, applying the method described above to each sperm cell and determining its fertility potential; and then selecting each sperm cell that has a fertility potential that meets a standardized criteria for selection of sperm cells in the IVF procedure. In other words, selecting a sperm cell that has a combined fertility potential score indicative of the DNA fragmentation condition and the condition(s) applied by the standardized criteria.

It is noted that the fertility potential of a sperm cell can be expressed as a fertility potential score basically reflecting the DNA fragmentation level of the sperm cell. In some embodiments, the fertility potential score may also incorporate and reflect the fact that the sperm cell additionally satisfies one or more criteria, such as the WHO2010, or any other relevant criteria, including criteria derived from the WHO2010 criteria.

Figure 2:
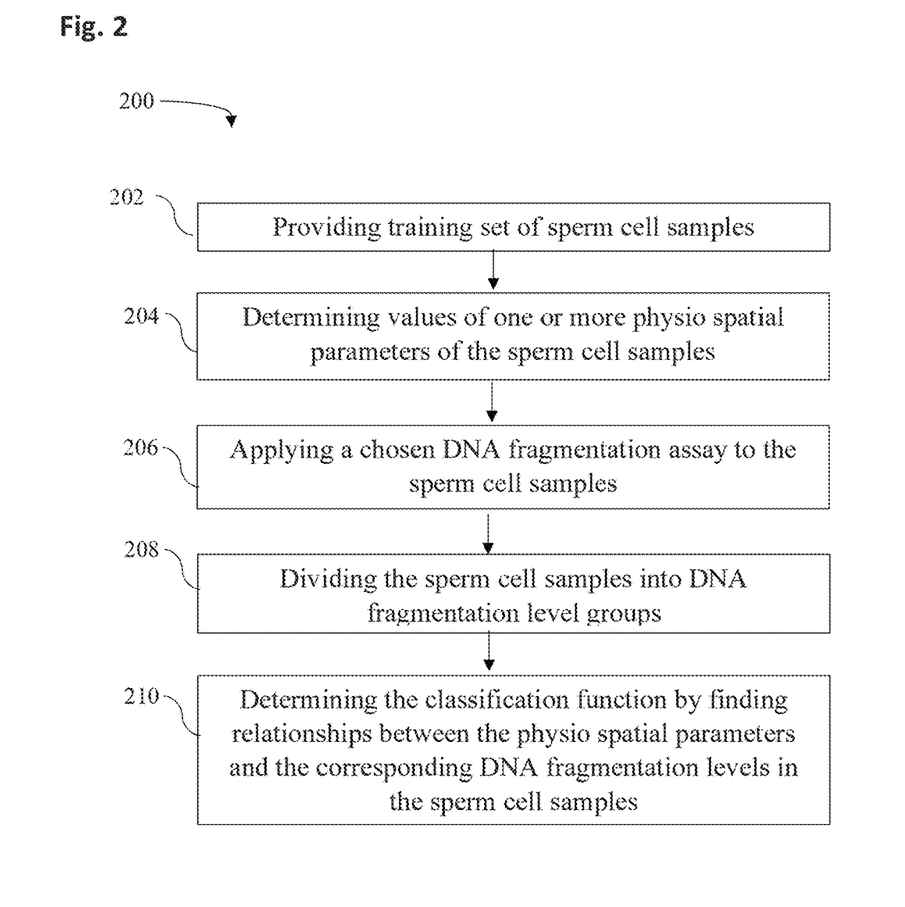
FIG. 2 illustrates a method for building a classification function for use in evaluating fertility potential of a sperm cell, according to some embodiments of the invention.

Reference is made to FIG. 2 illustrating a non-limiting example of a method 200 for building a classification function (operation) correlating between one or more physio spatial parameters of a sperm cell and a chosen DNA fragmentation distribution, in accordance with some embodiments of the present invention.

In step 202, a training set of sperm cell samples is provided. This step includes isolating the sperm cells and fixating them (thus, the sperm cells are no longer alive), possibly with the help of slides.

In step 204, one or more physio spatial parameters of interest in the sperm cell samples are determined utilizing a measurement technique suitable for acquiring the parameters of interest without staining the sperm cells. Specifically, according to the invention the measurement technique is based on quantitative phase microscopy. The physio spatial parameters are measured using the measurement technique with which the living, non-fixated and non-stained, sperm cell will be subjected to according to the method 100. Computer assisted techniques can be utilized to analyze the measurement results and determine the values of the physio spatial parameters. The results are saved for later access and further analysis.

In step 206, the training samples of the sperm cells are subjected to a DNA fragmentation assay in order to determine the DNA fragmentation level of the sperm cells and/or the different organelles. In one particular case, exemplified below, the DNA fragmentation assay used is Acridine Orange staining. The DNA fragmentation level can be assessed by imaging the stained samples, e.g. using confocal microscopy.

In step 208, the training samples of the sperm cells are divided into DNA fragmentation level groups according to the DNA fragmentation distribution determined by the DNA fragmentation assay. The division into groups can be physio spatial parameter specific or can involve a plurality of physio spatial parameters (e.g. a difference, addition, multiplication, between different physio spatial parameters).

In step 210, relationships between the physio spatial parameters and the DNA fragmentation levels are determined and a database is built. Comparison and differences between the groups can be evaluated using known statistical analysis. These relationships form the classification function to be applied to a living stain-free sperm cell, which by measuring its one or more relevant physio spatial parameters its DNA fragmentation state (level) can be determined, thus teaching about its fertility potential.

Figure 3A:
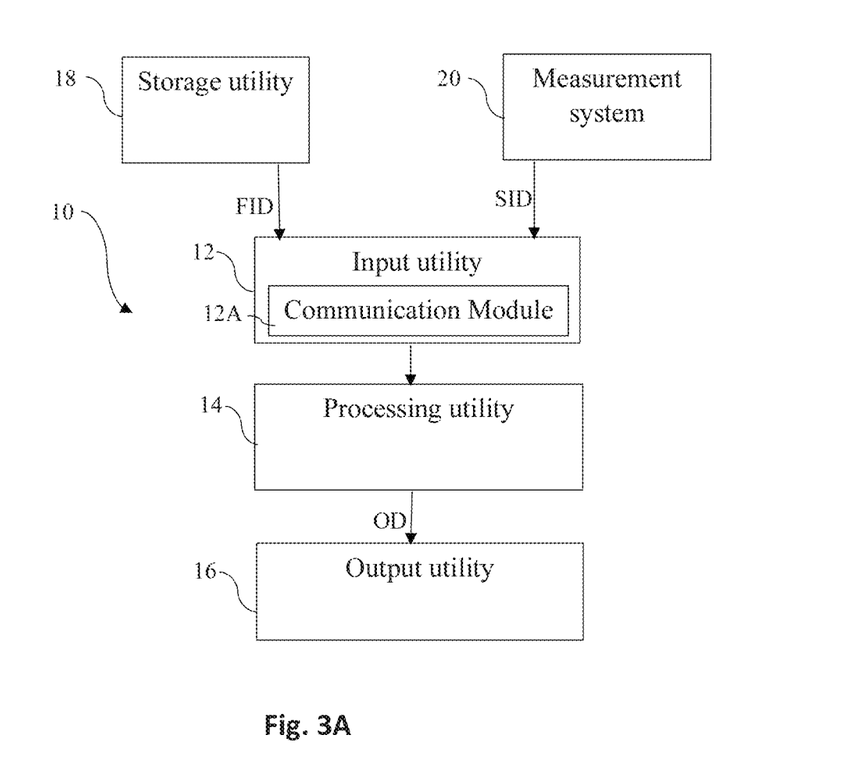
FIGS. 3A-3B illustrate systems for evaluating fertility potential of a sperm cell and selection of suitable sperm cells, according to some embodiments of the invention.

Reference is made to FIG. 3A illustrating a non-limiting example of a system 10 for evaluating fertility potential of a living sperm cell, according to some embodiments of the invention. the system 10 is configured and operable, inter alia, to execute the method 100 and/or 200.

In general, the system 10 is a computerized system essentially including, inter alia, the following utilities: an input utility 12, a processing utility 14, and an output utility 16. In some embodiments, the system 10 can further include other utilities or systems as will be further described below.

The input utility 12 is configured and operable to receive first input data FID including a predetermined classification function correlating between one or more physio spatial parameters of sperm cells and DNA fragmentation distribution in sperm cells, and second input data SID indicative of the one or more physio spatial parameters of the living sperm cell. In general, the first input data FID can be stored in a storage utility 18, which can be for example cloud-based storage, and which can be accessed by the input utility 12 whenever needed. To this end, the input utility 12 may include a communication module 12A configured and operable to access the storage utility 18 and retrieve the first input data FID therefrom. Alternatively, in some exemplary embodiments, the storage utility 16 may form part of the input utility 12 or the system 10 (this option is not shown in the figure).

The second input data SID is provided by a measurement system 20, such as a QPM or IPM, which is configured to communicate with the input utility 12 (e.g. via the communication module 12A). The second input data SID can be furnished to the input utility 12 on-line (i e immediately during/after measurement or can be stored in a memory of the measurement system 20 or in another storage utility (e.g. cloud-based, e.g. storage utility 18) to be accessed afterwards when needed by the input utility 12. In some exemplary embodiments of the invention, the system 10 may include the measurement system 20.

The processing utility 14 receives the first and second input data from the input utility 12 and processes the first and second input data to thereby generate output data OD indicative of the fertility potential of the living sperm cell under inspection. In some exemplary embodiments, the output data OD includes one or more of the following: data indicative of DNA fragmentation level of one or more parts (organelles) of the sperm cell, the DNA fragmentation level being a discreet value, a range of values, or a yes/no decision; and/or data indicative of fertility potential (a fertility potential score) being either a discreet value or a yes/no decision. As appreciated, the processing utility 14 is configured and operable to execute the step 106 of method 100 described herein-above.

In some embodiments, the processing utility 14 may be further configured and operable to determine whether the living sperm cell satisfies and/fulfils a standardized criteria for selection of sperm cells in a fertilization procedure. The standardized criteria may, for example, include criteria from World Health Organization (WHO) laboratory manual(s) for the examination and processing of human semen, e.g. the WHO2010 manual. For this purpose, the processing utility 14 may utilize one or more of the following: the one or more physio-spatial parameters of the sperm cell, kinetic measurements indicative of the sperm cell mobility (of one or more organelles) provided to the system 10 by a suitable measurement system (not specifically described herein), or other parameters indicated in the standardized criteria.

The output utility 16 is configured and operable to receive the output data OD and transmit this data in a meaningful way to a user of the system, either in visual or audible fashion or other suitable way. To this end, the output utility 16 includes a display, a speaker or other suitable utilities/modules. Additionally, the output utility 16 may be configured to send the output data OD to the storage utility 18 to be used for updating and optimizing the classification function.

It should be noted that, in some exemplary embodiments, the system 10 can also be configured to execute the steps of method 200. Alternatively, the classification function can be readily available (being prepared beforehand), to be accessed and used by the system 10 for executing method 100. When configured to execute method 200, the input utility 12 is configured and operable to perform step 202 by accessing a database of the training set of sperm cell samples, and the processing utility 14 is configured to execute the steps 204-210 and determine the classification function. The output utility 16 can then transmit the classification function to a storage utility (e.g. storage utility 18) to be accessed and used for executing method 100.

It is noted that some of the above features of the different utilities of system 10 are described only briefly because these features and capabilities are known in the art. However, this should not be interpreted in a way that limits the inventive features of the invention as described herein.

Figure 3B:
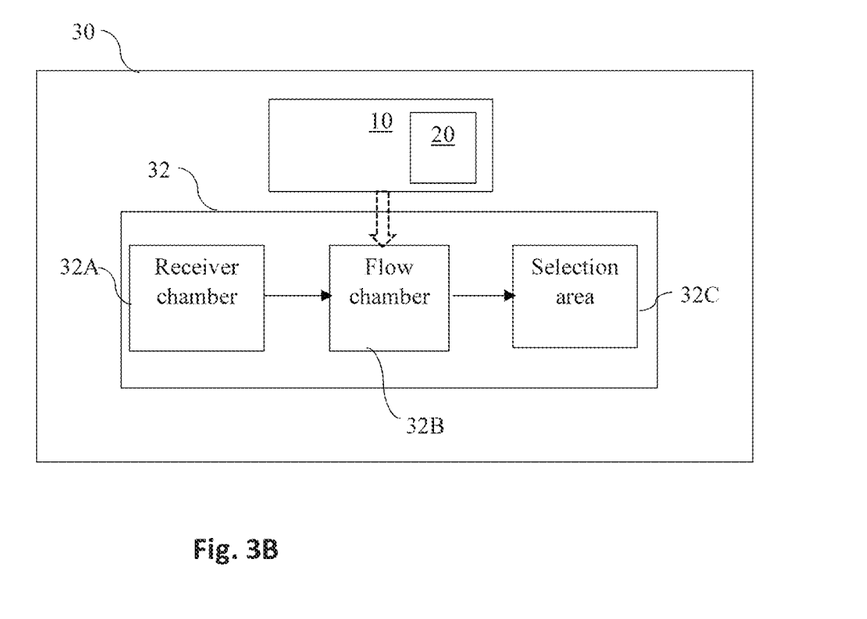

Reference is now made to FIG. 3B illustrating a non-limiting example of an apparatus 20 for use in an in vitro fertilization (IVF) procedure.

As shown, the apparatus 30 includes the system 10 for evaluating fertility potential of a living sperm cell.

The apparatus also includes a sorting system 32 configured and operable to: receive a plurality of living sperm cells, individually enable evaluating the fertility potential of each of the living sperm cells; and individually select one or more of the living sperm cells that meet a predetermined fertility potential score. Accordingly, in the shown example, the sorting system 32 includes a receiver chamber 32A configured for receiving a plurality of living sperm cells, e.g. in the form of a semen. A flow chamber 32B is configured to enable flow of the sperm cells, preferably one sperm cell at a time, to enable measuring the one or more physio-spatial parameters of the sperm cell by the measurement system 20, while moving inside the flow chamber 32B. After decision is made with regard to the fertility potential score of the sperm cell by the system 10, the sorting system 32 also includes a selection area 32C in which the selected sperm cells (fulfilling the predetermined fertility potential score) are chosen, e.g. by forcing them to flow in a specific direction, or through a specific outlet port, whereas the non-selected sperm cells (that do not satisfy the predetermined fertility potential score) are forced to flow in another direction, e.g. through a different outlet port.

Reference is now made to FIGS. 4-7 illustrating a non-limiting example of an experiment conducted by the inventors in accordance with the principles of the invention.

Semen samples were obtained from six childless sperm donors in their twenties. After ejaculation, the semen was liquefied at room temperature for 30 minutes and then sperm cells were isolated using the PureCeption Bi-layer kit (Origio, Målov, Denmark) in accordance with manufacturer instructions in order to obtain mature sperm cells. The upper phases were gently removed and the pellet was resuspended in 5 ml of modified human tubal fluid (HTF) medium (Irvine Scientific, CA, USA) and centrifuged again at 500 g for 5 minutes. Next, the supernatant was discarded and the pelleted sperm cells were resuspended in 0.1 ml HTF. To enable measurement of the same cell by two microscopy systems, the sperm cells were fixed without changing their morphology by drop addition of 10 ml of 3:1 methanol to acetic acid solution. After 5 minutes at room temperature, the cells were centrifuged at 800 g for 5 minutes, the supernatant was discarded, and the pellet was resuspended in 0.2 ml of fixative solution.

Figure 4A:
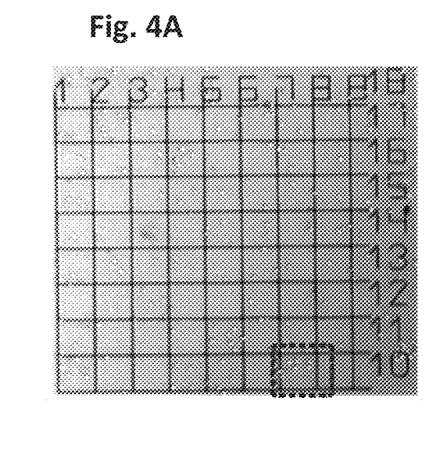
FIGS. 4 to 7 illustrate an exemplary experiment conducted in accordance with the principles of the invention.
Figure 4B:
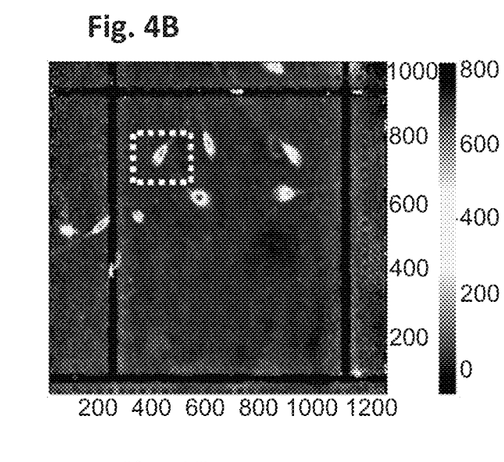
Figure 4C:
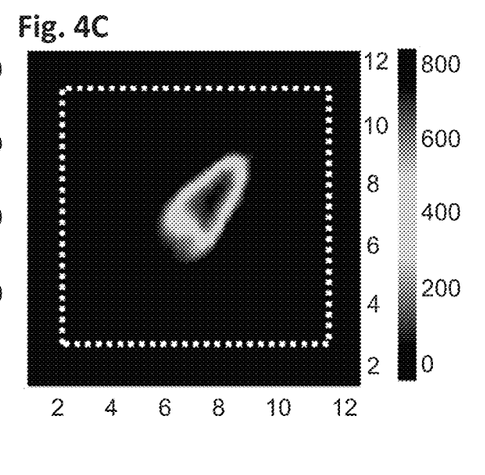

As shown in FIG. 4A, a 60 mm×20 mm #1 cover slip was used with 9 laser-engraved tables, each table containing 64 squares of 80 µm×80 µm each. The slides were rinsed with methanol before use, 10 µl of the fixed sperm cell solution was placed on the engraved grid and kept in a fume hood overnight to ensure the evaporation of the fixative solution. A single slide contained cells from a single donor.

The fixed sperm cells were imaged under 60× magnification using an IPM system designed by the inventors. The camera in the output of the IPM system captures an interferogram that is digitally processed into an OPD map of the sample by digital spatial filtering and phase unwrapping algorithm; a stain-free quantitative image of the sperm representing a cell average refractive index of the cell and thickness at all spatial points was obtained.

The stain-free OPD images of each cell were evaluated by an expert embryologist (M.L.) in accordance with the WHO guidelines. The embryologist evaluated and individually graded each sperm cell by head shape, acrosome size, cytoplasmic vacuole and cytoplasmic droplet presence, and midpiece form.

Then, computer assisted evaluation of sperm cell morphological parameters was performed.

The isolation and evaluation of sperm cells was performed using a Matlab algorithm designed by the inventors for this purpose.

The output of this procedure was the OPD map of the cell head, nucleus and acrosome, in addition to many parameters that can be calculated based on the OPD, such as dry mass, mean anterior-posterior difference, head, acrosome, and nucleus areas, and head OPD variance. The mean anterior-posterior difference was calculated by dividing the isolated head OPD image into two equal halves lengthwise, the anterior and posterior halves of the head. Following this, the mean OPD values of these halves were calculated and the mean posterior OPD was subtracted from the mean anterior OPD in order to get the final mean anterior-posterior difference.

The dry mass of the cell can be determined from the OPD using the following parameters. It was previously determined by the inventors that the average dry mass of a sperm head was $DM=7.51\pm1.03\cdot10^{-12}$ gram, and the average refractive index of a sperm head was $n_c=1.515\pm0.046$. This was achieved by comparing the OPD maps with the exact height measurements of the same cells using an atomic force microscope (AFM). Based on the following Equation, the volume (V) of the cells can be calculated:

$$V = \text{Area} * \text{Thickness} = \text{Area} * \frac{OPD}{n_c - n_m}. \qquad \text{Equation 2}$$

From the AFM measurements, the average volume of the cells can be obtained and the average concentration of dry mass density in sperm cells is calculated; $\rho=M/V=1.013\cdot10^{-21}$ gram/nm$^3$=$1.013\cdot10^3$ gram/liter. This value was then used to calculate the dry mass of each cell or its compartment by multiplying the volume calculated by Equation 2 by $\rho$.

$$DM = \text{Area} \cdot \overline{OPD} \cdot \rho \qquad \text{Equation 3}$$

The fixed sperm cells, previously imaged by IPM, were then stained by AO using the Tejada's method. In short, the slides were exposed to AO (0.19 mg/ml, pH 2.5) for 5 minutes Staining solution was prepared daily from a stock solution consisting of 1 mg AO in 1 L of deionized water, and stored in the dark at 4° C. To prepare the staining solution, 10 mL of the stock solution was added to 40 mL of 0.1 M citric acid and 2.5 mL of 0.3 M $Na_2HPO_4$ $7H_2O$. No loss of sperm cells was detected after staining with AO.

After staining, the slides were rinsed in a stream of deionized water for 5 minutes, air dried and imaged within two hours by a confocal fluorescence microscope. Each engraved table of 8×8 squares was imaged using a 25×, 1.4 numerical aperture microscope objective. The cells were excited using light at wavelengths 477-488 nm, and emission was filtered between 572-668 nm for the red and 505-550 nm for green. Each arbitrary fluorescent cell was blindly evaluated by the experimentalist (L. K.) in a color scale of 1 (red) to 5 (green), and the color was incorporated into the database obtained by the algorithm and the embryologist.

For each parameter, determined either by the algorithm (e.g. cell area, dry mass) or the embryologist (e.g. head shape), the sperm cells were divided into groups according to their AO colors. For the quantitative parameters, determined by the algorithm, the mean of each of the parameters was calculated and presented in a column chart with error bars representing the standard error.

For the embryologist-determined information (binary classification), the percentage of normal cells was calculated, as determined by the embryologist in this particular parameter in each of the AO groups. In this experiment the significance of the differences between the groups was established by the $\chi^2$ test.

In computer assisted evaluation of sperm cell morphological parameters, the differences between groups were examined using analysis of variance (ANOVA), complimented by Tukey's multiple comparisons test for comparison between the different groups. The differences between groups were considered statistically significant if the probability, p, for the associated value was smaller than 0.05. Slope analysis was conducted wherever the changes in a particular parameter were consistent over 4 fragmentation groups. The slope was calculated by linear regression. The significance of the direction of the slope is shown by the 95% confidence interval. All calculations were performed using IBM SPSS STATISTICS 24.0.0.1. The statistical analysis was generated by IBM SPSS STATISTICS 24.0.0.1. The charts were generated by the GraphPad Prism v.7.

As mentioned above, sperm cells were washed and fixed on a gridded slide. FIG. 4A shows a fluorescent image of the fixed sperm cells after staining with AO, superimposed with BFM image. Before the AO staining, the cells, immobilized on the grid, were imaged using IPM, as in the example shown in FIGS. 4B and 4C, and analyzed by the algorithm as well as by the embryologist. Out of 1699 cells and cell fragments that were identified by the computer, 1336 cells were confirmed as sperm cells by an embryologist, and only these cells were used in the statistical analysis. The number of sperm cells from each donor is 139, 98, 106, 298, 254 and 387 cells.

Figure 4D:
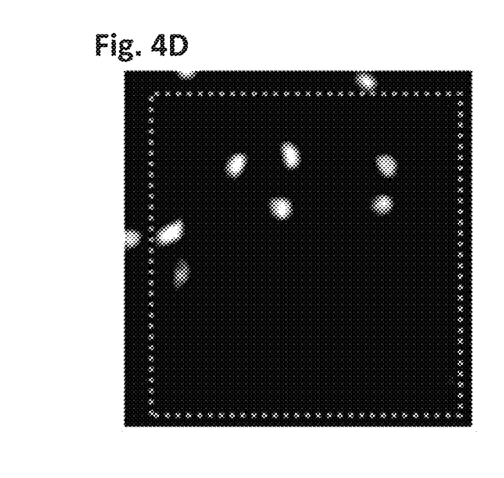
Figure 4E:
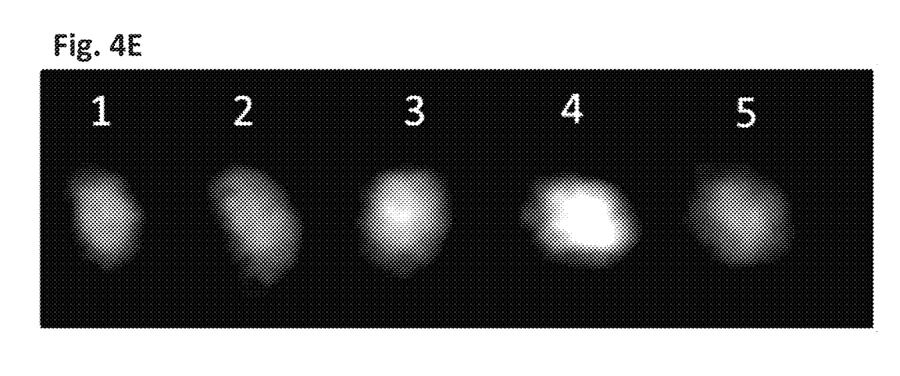
Figures 5A, 5D:
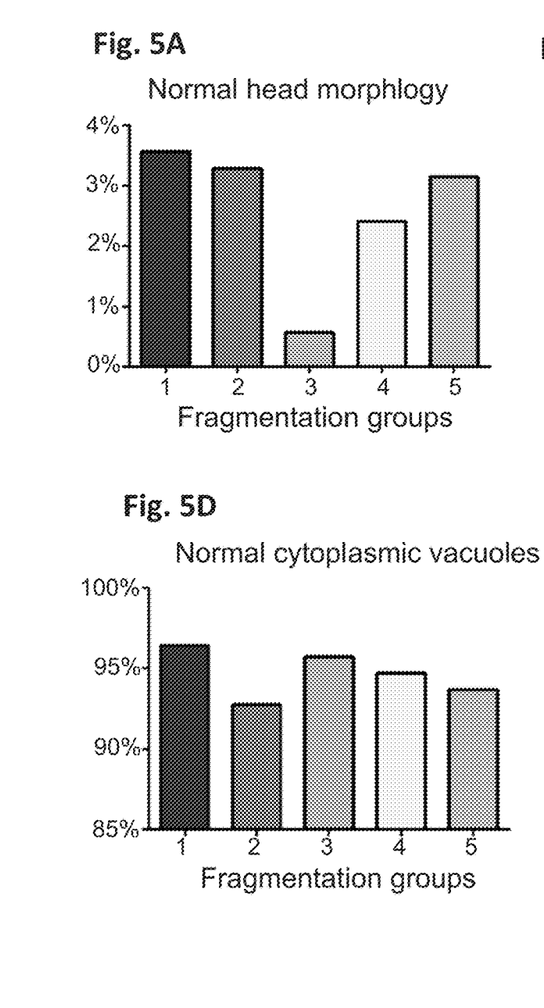
Figure 5B:
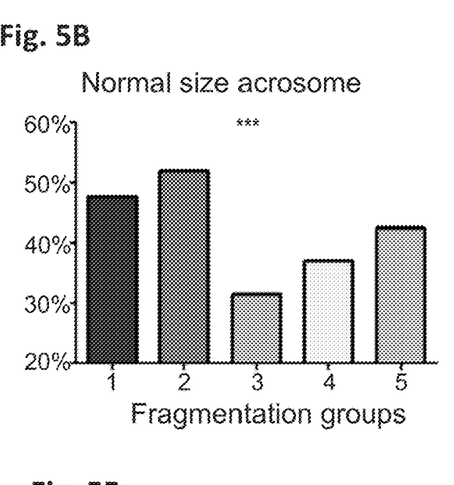
Figure 5C:
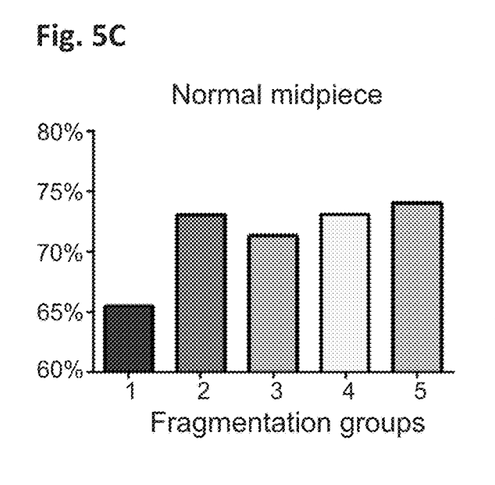
Figure 5E:
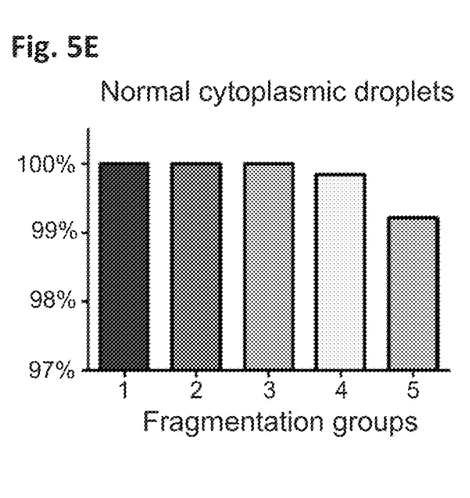

After the cells were imaged using IPM, the same slides were stained by AO and imaged using the confocal fluorescence microscope as exemplified in FIG. 4D. The color of each cell was then determined, with the color scale being from 1-5, with red being 1 and green being 5 as illustrated in FIG. 4E. It is noted that this color scale is used in all the FIGS. 4 to 7, such that the group 1 means the most red and group 5 means the most green whereas groups 2 to 4 mean a mixture of red and green with a a gradual move from red to green. Because the overall color of the cell is determined by the sum of the green and red colors, the color of the cells can be regarded as a scale that reflects the proportion between dsDNA to ssDNA (single stranded or fragmented DNA) and RNA, as well as the overall amount of nucleic acids. The number (and the percentage) of cells in each color group, from the most fragmented to the least fragmented was—group 1: 84 cell (6.3%), group 2: 152 cells (11.4%), group 3: 349 cells (26.1%), group 4: 624 cells (46.7%) and 5 group: 127 cells (9.5%).

According to the WHO guidelines for the morphological evaluation of smeared and stained semen, there are 5 criteria by which a sperm is determined as having "normal morphology". In order for a semen sample to be considered normal, at least 4% of the sperm cells must have a normal morphology. The criteria are: an acrosome that composes of 40% to 70% of the sperm head area, typical head shape, no excessively large external cytoplasmic droplets, no more than 2 small cytoplasmic vacuoles (<20% of head area) and only in the acrosome area, and a straight and smooth midpiece. Since stain-free IPM and stain-based BFM yield comparable results in sperm analysis, these parameters were evaluated by an embryologist examining the stain-free IPM images, and the fraction of cells that were found to be normal in each criterion, respectively, were classified according to the color group, in order to determine the number of cells at each of the five different levels of DNA fragmentation, as shown in FIGS. 5A-5E.

As can be seen in FIGS. 5A-5E, the percentage of cells presenting normal morphology in the categories of head morphology (FIG. 5A), acrosome size (FIG. 5B), midpiece (FIG. 5C), cytoplasmic vacuoles (FIG. 5D), and cytoplasmic droplets (FIG. 5E) is plotted. $\chi^2$ test shows a statistically significant difference in the distribution of normal cells between different fragmentation groups. Statistically significant difference was found in "acrosome size" category (p<0.001). The "acrosome size" rises gradually from group 3 to group 5.

According to other additional criteria evaluated—Head morphology, midpiece, cytoplasmic vacuoles and cytoplasmic droplets, it was found that the differences between the percentage of normal cells in each color group are not statistically significant.

FIGS. 6 and 7 show 2D and 3D criteria calculated based on the isolated cell OPD maps.

Figure 6A:
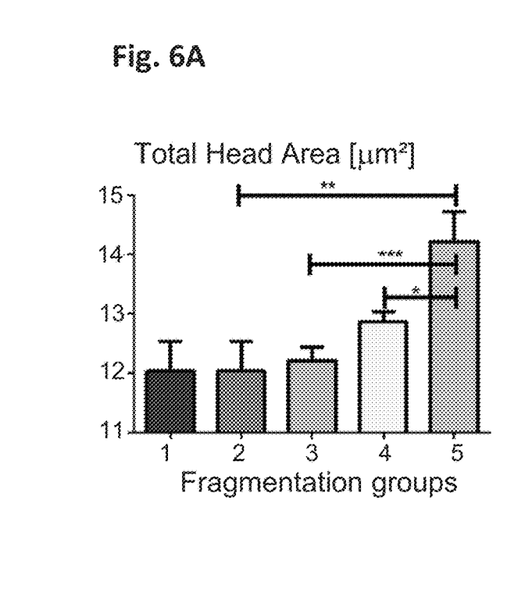
Figure 6B:
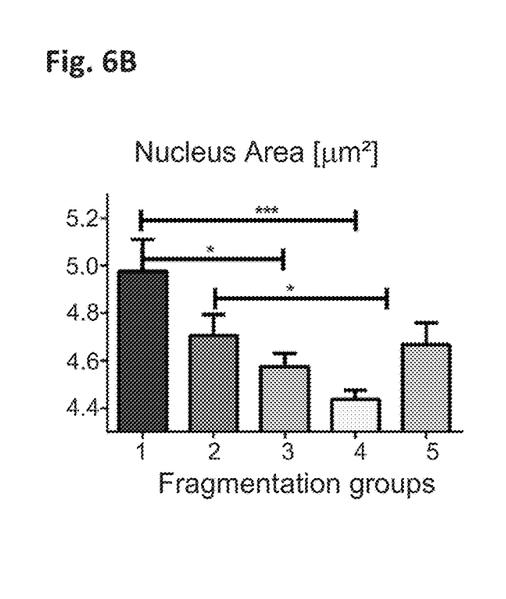
Figure 6C:
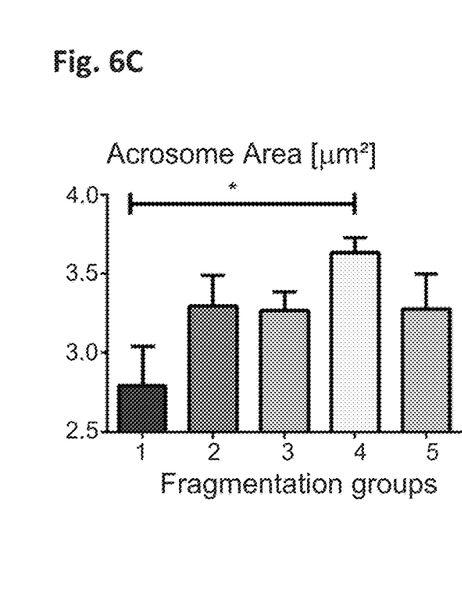

In FIGS. 6A-6C, evaluation of morphologic parameters in different DNA fragmentation groups is shown. In each fragmentation group, the mean projection area of the: sperm head (FIG. 6A), the nucleus (FIG. 6B) and the acrosome (FIG. 6C) is presented. The values were automatically calculated from the IPM images. The error bars represent standard error of the mean value. ANOVA test was used to determine statistically significant differences (*p <0.05, *** p<0.001).

Figure 7A:
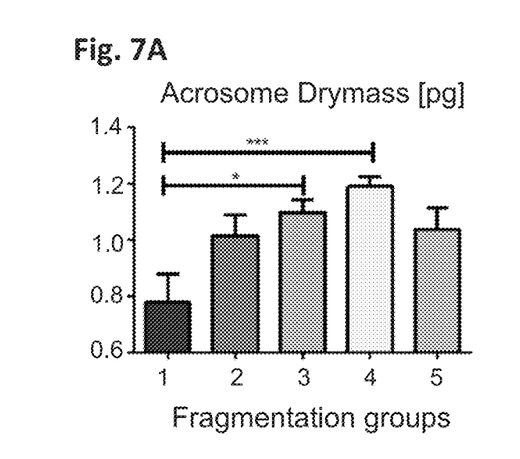
Figure 7B:
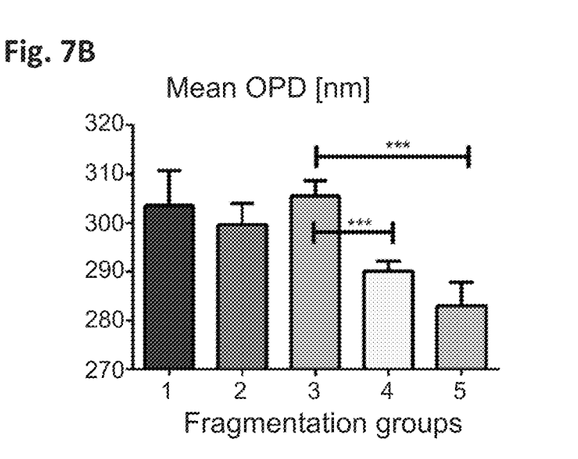
Figure 7C:
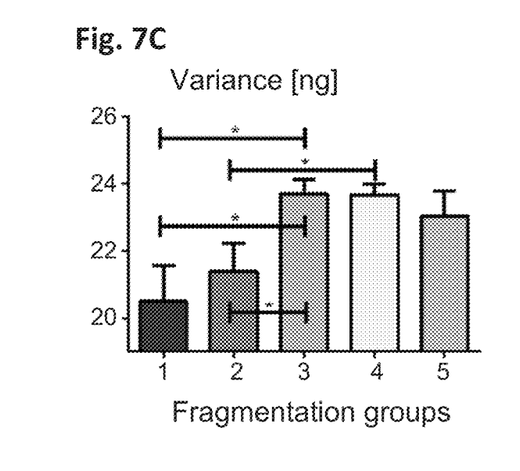
Figure 7D:
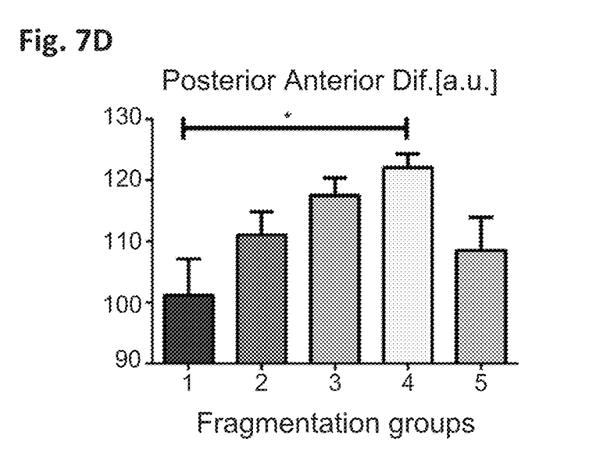

In FIGS. 7A-7D, evaluation of OPD-related parameters in different DNA fragmentation groups is shown. FIG. 7A illustrates the mean dry mass of the acrosome expressed in Pico-gram. FIG. 7B illustrates the mean OPD in nanometer. FIG. 7C illustrates the variance of the OPD in nanometer. FIG. 7D illustrates the anterior-posterior difference, representing the difference in OPD between the rear half and the front half of the cell. The error bars represent standard error of the mean value. ANOVA test was used to determine statistically significant differences (*p<0.05, *p<0.01, *p<0.001).

In exanimating the different morphologic parameters, it is observed that overall, head area (FIG. 6A) increased gradually from groups 3 to 5, the nucleus area (FIG. 6B) decreased from group 1 to 4 at a slope of $-0.09725$ $\mu m^2$ per group (95% confidence interval (CI) $-0.1520$ to $-0.04248$), and acrosome area (FIG. 6(C)) increased from group 1 to 4 with the decreased fraction of fragmented DNA.

The examination of selected dry mass and OPD dependent parameters shows an increase of acrosome dry mass (FIG. 7A) with the increase of un-fragmented DNA from group 1 to 4 with slope of 0.07505 µg per group (95% CI 0.02898 to 0.1211). The mean OPD representing the mean thickness of the cells (FIG. 6B) declines from group 3 to 5.

Other criteria can be useful to distinguish between the different fragmentation groups, for example the OPD variance (FIG. 7C) and the mean anterior-posterior (FIG. 7D). OPD variance is obtained by calculating the statistical variance of the OPD values on the entire cell area. OPD variance is highest in groups 3 and 4. The mean anterior-posterior difference (FIG. 7D) is a metric developed by the inventors and compares the average OPD (FIG. 7B) of the anterior and posterior (FIG. 7D) halves of the sperm head, it shows a gradual increase from group 1 to 4 with slope of 3.282 (95% CI 0.3677 to 6.197). This trend is reversed in group 5, emphasizing the difference of these cells from group 4.

As can be seen from the experimental results, sperm cells in the most fragmented groups (groups 1 and 2) are characterized by a large nuclear area (FIG. 6B) and small acrosomes (FIG. 6C). The medium fragmented groups (groups 3 and 4) are characterized by a small and compressed nucleus (FIG. 6B). Group 4 is distinguished from group 3 by its larger acrosomes (FIG. 6B) and lower mean OPD (FIG. 7B). Group 5 is characterized by the largest head area (FIG. 6A) and a large acrosome (FIG. 7A) similar to that of cells in group 4. However, cells in group 5 have a smaller mean OPD (FIG. 7B) than cells in group 4. Overall, in this experiment, no single criteria can distinguish between the different fragmentation groups, and only a combination of the different criteria can reliably predict the fragmentation status.

AO staining was used as a verification method to IPM. There are several direct methods to test DNA fragmentation in sperm. The two most prevalent methods in the clinical setting are sperm chromatin structure assay (SCSA) and the TUNEL assay. For the routine diagnosis of patients, these methods are used with flow cytometry. SCSA uses AO staining, resulting in DNA fragmentation index (DFI), which corresponds to the presence of sperm cells that show high levels of red staining The current threshold for abnormal DFI is 25% of sperm cells. SCSA also identifies a subpopulation of cells that emits high level of green light, which possesses high DNA stainability (HDS), but this population has no effect on the DFI and thus it is not used in clinical decisions. TUNEL tests DNA fragmentation by binding and labeling the terminal ends of the nucleic acids, and can be performed by microscopy or flow cytometry. In contrast to SCSA, TUNEL can detect DNA damage caused by oxidative stress. A recent study suggested that during the sperm isolation process, the cells are damaged after long exposures by metals found in the nano-particles that are used for sperm cell isolation. This damage is detectable only with TUNEL and not with AO. In the present example, the cells were exposed to nano-particles for only 20 minutes; thus, the DNA damage is relatively small The AO method was chosen, in this non-limiting example, since this method enables to divide the cells into 5 different groups, including group #5, the HDS group, which is characterized by dsDNA but with a difficient DNA packing. In addition, the AO assay was reported to be more effective in detecting small fragmentations in the DNA than TUNEL, because in the AO assay the stain has better access to the compact sperm chromatin.

Although the different DNA fragmentation assays are efficient in diagnosing patients with high percentage of defective sperm cells, they cannot be used to select an individual sperm for ICSI, because they require the cell to be killed for the test to be performed.

An indirect indication for the DNA fragmentation is the lack of acrosome reaction or morphological deformities in sperm head such as globozoospermia (a condition characterized by abnormal sperm morphology, including small or absent acrosome).

The experiment results indicate that fragmentation groups 3 and 4 showed a larger acrosome compared to groups 1 and 2. The correlation between DNA fragmentation and acrosomal deficiencies is explained by defects during the late spermatogenesis. At this stage in sperm development, somatic cell histones are replaced by protamines: proteins necessary for the proper packaging of DNA during spermiogenesis as well as the protection of the sperm from DNA damage and, at the same time, the acrosome is formed. Thus, sperm cells that underwent defected spermiogenesis are likely to present both defected DNA and defected acrosomes.

No statistical link between midpiece morphology and DNA fragmentation was clearly demonstrated in this example. The midpiece is the organelle responsible for cell motility, an abnormal midpiece is correlated with impaired motility and reduced fertilization rate during IVF. In general, it has been long shown that sperm motility is correlated to DNA fragmentation; however, DNA fragmentation was reported as a better predictor for conception than progressive morphology in the context of ICSI, making the selection process prone to error.

Further, in this example, statistically significant differences were not observed in the prevalence of cytoplasmic vacuoles in sperm cells with different DNA fragmentation levels. Cytoplasmic vacuoles in sperm cells are subtle morphological nuclear malformations caused by DNA condensation defects in the nucleus, and is one of the structures that can easily be observed using IMSI. In that method, sperm cells are examined under a high-magnification (at least 6000×, most of which is a digital magnification, which is convenient for view by the observer on a screen) DIC microscope. Using IMSI, several cellular characteristics, which cannot be observed using a regular ICSI microscope, are distinguished. These include the presence of cytoplasmic vesicles and the head detailed shape. The acrosome can also be viewed in this method; however, its exact size and mass cannot be quantified using DIC microscopy. However, the clinical significance of cytoplasmic vesicles is a topic of debate in the clinical community Overall, IMSI was found by meta-analysis to increase implantation and pregnancy rates as well as to decrease the chances of miscarriage in couples that had at least one failed ICSI attempt. The moderate improvement in fertilization and pregnancy rates using the IMSI method suggests that improved sperm visualization can improve overall results. Thus, the use of QPM, which is a fully quantitative imaging method for sperm evaluation, further improves the selection of fertile sperm cells, especially as staining is not possible.

Trend-correlation is demonstrated between various parameters that can be accurately quantified only by QPM and the ratio of ssDNA to dsDNA in sperm cells as observed under fluorescent microscopy after staining the same cells with AO. A single color was not used as a threshold between sperm cells with fragmented or un-fragmented DNA. The benefit in dividing the cells to five different groups by color is that it enables to examine the morphologic characteristics of each group separately.

After an embryologist examined the OPD maps of the different groups using the various WHO criteria: head morphology, acrosome size, cytoplasmic vacuoles, midpiece integrity and cytoplasmic droplets, a gradual increase in the percentage of "normal" cells from group 3 to 5 in the category of acrosome size is observed.

Following the digital examination of the OPD maps of the sperm cells and their comparison to the different fragmentation groups, differences in the values of parameters that can only be calculated by QPM, such as the mean OPD, the size of the acrosome or the mean posterior anterior difference, amongst the different groups are observed. In examining the cells by QPM, sperm cells in group 5, the cells that shined in the bright green, are distinct from all other cell groups. As shown in the results above, these cells present significantly larger head area compared to groups 3 and 4. This population of cells are suspected to be HDS, a population of sperm cells with defected DNA arrangement.

Limitations of the exemplified experiment include the small number of donors and the fact that the donors are not known to have fertility problems, making them unrepresentative of men in need of assisted reproduction technologies. In addition, in order to image the same cells with two microscopy systems (IPM and confocal fluorescence microscopy), the cells were fixed. IPM is meant to be performed for live unfixed cells. Since the fixation procedure did not change the cell morphology, it is hypothesized that IPM imaging of live cells in medium will yield similar results in detecting DNA fragmentation.

In conclusion, IPM imaging can produce a detailed and quantitative morphological map of sperm cells. This map can be used to predict the DNA fragmentation levels of individual living cells without staining

The invention claimed is:

1. A method for evaluating fertility potential of a living sperm cell, the method comprising:

deriving, from at least one of two-dimensional and three-dimensional optical path delay image data of a non-stained living sperm cell, data indicative of one or more predetermined physio spatial parameters of the non-stained living sperm cell being inspected, by performing at least one of quantitative phase microscopy (QPM) and interferometric phase microscopy (IPM) measurement on said living sperm cell after passing said living sperm cell through one of the following assays: (a) sperm density gradient, (b) swim-up, (c) hyaluronic acid binding, and (d) magnetic sorting using annexin V microbeads, wherein each of said one or more predetermined physio spatial parameters comprises one or more of the following: surface area of the living sperm cell or an organelle thereof; dry mass of the living sperm cell or of an organelle thereof; an average optical path delay of a certain surface area on the living sperm cell or of an organelle thereof; a variance of optical path delay being calculated of surface area of a part of all of the living sperm cell or of an organelle thereof; a subtraction between an average optical path delay calculated upon an anterior portion of the head of the living sperm cell and an average optical path delay calculated upon a posterior portion of the head of the living sperm cell, each of said anterior and posterior portions comprising between 40 and 60 percent of the surface area of the head of the living sperm cell;

providing said data indicative of said one or more predetermined physio spatial parameters as input data to a classifier of the fertility potential of the non-stained living sperm cell based on a DNA fragmentation level of the living sperm cell, said classifier being defined by a predetermined classification function being a correlation function correlating between one or more predetermined physio spatial parameters of sperm cells and DNA fragmentation distribution in sperm cells, said classification function being predetermined based on a dataset of training sperm cell samples each characterized by measured one or more predetermined physio spatial parameters and respective DNA fragmentation levels derived from a DNA fragmentation assay;

applying said classification function to said one or more predetermined physio spatial parameters of the living sperm cell being inspected and determining an estimated DNA fragmentation level, inside said DNA fragmentation distribution, in said living sperm cell being inspected, the DNA fragmentation level being indicative of the fertility potential of the living sperm cell.

2. The method according to claim 1, wherein said DNA fragmentation distribution is a binary distribution comprising two levels of DNA fragmentation being respectively indicative of fertile and non-fertile conditions of a sperm cell.

3. The method according to claim 1, wherein said DNA fragmentation distribution is a multi-class distribution comprising at least three levels of DNA fragmentation being indicative of respective fertility potential levels of a sperm cell.

4. The method according to claim 1, wherein said DNA fragmentation distribution is defined based on one of the following DNA fragmentation assays: (a) acridine orange (AO), (b) terminal deoxynucleotidyl transferase-mediated deoxyuridine triphosphate-nick end labeling (TUNEL), (c) single cell gel electrophoresis (SCGE), (d) sperm chromatin dispersion (SCD), and (e) sperm chromatin structure (SCSA).

5. The method according to claim 1, wherein said organelle comprises at least one of the following: head, nucleus, acrosome and tail of the living sperm cell.

6. The method according to claim 1, wherein said sperm cell is a washed sperm cell.

7. The method according to claim 1, further comprising determining whether said living sperm cell fulfils a standardized criteria for selection of sperm cells in a fertilization procedure.

8. The method according to claim 7, wherein said standardized criteria comprises criteria from World Health Organization (WHO) laboratory manual(s) for the examination and processing of human semen.

9. A method for use in an in vitro fertilization (IVF) procedure, the method comprising:

providing a plurality of sperm cells;

applying the method of claim 1 to each sperm cell and determining its fertility potential; and selecting each sperm cell that has a fertility potential that meets a standardized criteria for selection of sperm cells in the IVF procedure.

10. A system for evaluating fertility potential of a living sperm cell, the system comprising:

a measurement system configured to perform at least one of quantitative phase microscopy (QPM) and interferometric phase microscopy (IPM) measurements of a non-stained living sperm cell that has passed through one of the following assays: (a) sperm density gradient, (b) swim-up, (c) hyaluronic acid binding, and (d) magnetic sorting using annexin V microbeads, and derive, from at least one of two-dimensional and three-dimensional optical path delay image data of the non-stained living sperm cell, first data indicative of one or more predetermined physio spatial parameters of the non-stained living sperm cell being inspected, wherein each of said one or more predetermined physio spatial parameters comprises one or more of the following: surface area of the living sperm cell or an organelle thereof; dry mass of the living sperm cell or of an organelle thereof; an average optical path delay of a certain surface area on the living sperm cell or of an organelle thereof; a variance of optical path delay being calculated of surface area of a part of all of the living sperm cell or of an organelle thereof; a subtraction between an average optical path delay calculated upon an anterior portion of the head of the living sperm cell and an average optical path delay calculated upon a posterior portion of the head of the living sperm cell, each of said anterior and posterior portions comprising between 40 and 60 percent of the surface area of the head of the living sperm cell;
- a data input utility configured and operable for receiving a second data indicative of a classifier of the fertility potential of the non-stained living sperm cell based on a DNA fragmentation level of the living sperm cell, the classifier being defined by a predetermined classification function being a correlation function correlating between one or more predetermined physio spatial parameters of sperm cells and DNA fragmentation distribution in sperm cells, said classification function being predetermined based on a dataset of training sperm cell samples each characterized by measured one or more predetermined physio spatial parameters and respective DNA fragmentation levels derived from a DNA fragmentation assay;
- a processing utility configured and operable for processing said first and second data, the first data being provided as input to the classifier, determining an estimated DNA fragmentation level, inside said DNA fragmentation distribution, in said living sperm cell, the DNA fragmentation level being indicative of the fertility potential of the living sperm cell, and generating a corresponding output data; and
- a data output utility configured and operable to present the output data to a user of the system.

11. The system according to claim 10, wherein said measurement system is a quantitative phase microscopy system configured and operable to obtain said at least one of two-dimensional and three-dimensional image data of the living sperm cell indicative of optical path delay (OPD) of one or more organelles of said living sperm cell and enable determining said one or more predetermined physio spatial parameters of the living sperm cell.

12. The system according to claim 10, wherein said processing utility is further configured and operable for determining whether said living sperm cell fulfils a standardized criteria for selection of sperm cells in a fertilization procedure.

13. An apparatus for use in an in vitro fertilization (IVF) procedure, the apparatus comprising:
- a system for evaluating fertility potential of a living sperm cell according to claim 12; and
- a sorting system configured and operable to: receive a plurality of living sperm cells, individually enable evaluating the fertility potential of each of the living sperm cells, and individually select one or more of the living sperm cells that meet a predetermined fertility potential score.

14. A method for use in an in vitro fertilization (IVF) procedure, the method comprising:
- providing a plurality of non-stained living sperm cells;
- determining a fertility potential of each non-stained living sperm cell; and
- selecting each non-stained living sperm cell that has a fertility potential that meets a standardized criteria for selection of sperm cells in the IVF procedure;
- wherein said determining of the fertility potential of each non-stained living sperm cell comprises:
  - deriving, from at least one of two-dimensional and three-dimensional optical path delay image data of the non-stained living sperm cell, data indicative of one or more predetermined physio spatial parameters of the non-stained living sperm cell being inspected, wherein each of said one or more predetermined physio spatial parameters comprises one or more of the following: surface area of the living sperm cell or an organelle thereof; dry mass of the living sperm cell or of an organelle thereof; an average optical path delay of a certain surface area on the living sperm cell or of an organelle thereof; a variance of optical path delay being calculated of surface area of a part of all of the living sperm cell or of an organelle thereof; a subtraction between an average optical path delay calculated upon an anterior portion of the head of the living sperm cell and an average optical path delay calculated upon a posterior portion of the head of the living sperm cell, each of said anterior and posterior portions comprising between 40 and 60 percent of the surface area of the head of the living sperm cell;
  - providing said data indicative of said one or more predetermined physio spatial parameters as input data to a classifier of the fertility potential of the non-stained living sperm cell based on a DNA fragmentation level of the living sperm cell, said classifier being defined by a predetermined classification function being a correlation function correlating between one or more predetermined physio spatial parameters of sperm cells and DNA fragmentation distribution in sperm cells, said classification function being predetermined based on a dataset of training sperm cell samples each characterized by measured one or more predetermined physio spatial parameters and respective DNA fragmentation levels derived from a DNA fragmentation assay;
  - applying said classification function to said one or more predetermined physio spatial parameters of the living sperm cell being inspected and determining an estimated DNA fragmentation level, inside said DNA fragmentation distribution, in said living sperm cell being inspected, the DNA fragmentation level being indicative of the fertility potential of the living sperm cell.

* * * * *